United States Patent [19]

Tokuda et al.

[11] Patent Number: 4,794,954
[45] Date of Patent: Jan. 3, 1989

[54] APPARATUS AND METHOD FOR PREVENTION OF PULSATING FLOW IN LIQUID CHROMATOGRAPH

[75] Inventors: Toshio Tokuda, Kamakura; Tsunemi Tokieda, Yokohama; Norio Ishida, Kawasaki, all of Japan

[73] Assignee: Showa Denko Kabushiki Kaisha, Tokyo, Japan

[21] Appl. No.: 22,447

[22] PCT Filed: May 13, 1986

[86] PCT No.: PCT/JP86/00242
§ 371 Date: Jan. 13, 1987
§ 102(e) Date: Jan. 13, 1987

[87] PCT Pub. No.: WO86/06815
PCT Pub. Date: Nov. 20, 1986

[30] Foreign Application Priority Data

May 13, 1985 [JP] Japan .................................. 60-99640

[51] Int. Cl.⁴ .............................................. F16L 55/04
[52] U.S. Cl. .................................... 138/30; 210/198.2
[58] Field of Search ................ 138/30; 210/198.2, 349

[56] References Cited

U.S. PATENT DOCUMENTS

| | | | |
|---|---|---|---|
| 2,883,180 | 4/1959 | Moulton | 138/30 X |
| 4,024,061 | 5/1977 | Gatiss | 138/30 X |
| 4,222,414 | 9/1980 | Achener | 138/30 |
| 4,427,029 | 1/1984 | Charney et al. | 138/30 |
| 4,552,182 | 11/1985 | Graham | 138/30 |
| 4,587,993 | 5/1986 | Härtl | 138/30 |
| 4,629,562 | 12/1986 | Kercher | 138/30 X |

FOREIGN PATENT DOCUMENTS 57-5570    2/1982   Japan .
57-160060 10/1982   Japan .
58-72795   4/1983   Japan .

*Primary Examiner*—William A. Cuchlinski, Jr.
*Attorney, Agent, or Firm*—Sughrue, Mion, Zinn, Macpeak & Seas

[57] ABSTRACT

To prevent a pulsating flow in a column used for the liquid chromatograph, a flat liquid transferring chamber (6) provided in pressure vessels (1a, 1b) is partitioned by diaphragms (2a, 2b) on both flat sides thereof, and sealed compression chambers (5a, 5b) filled with a compressible substance are disposed facing the diaphragms.

2 Claims, 1 Drawing Sheet

APPARATUS AND METHOD FOR PREVENTION OF PULSATING FLOW IN LIQUID CHROMATOGRAPH

TECHNICAL FIELD

The present invention relates to an apparatus for liquid chromatograph, particularly to an apparatus and a method for the prevention of pulsating flow in the liquid chromatograph, wherein pulsations in the flow of liquid being transferred are eliminated.

BACKGROUND ART

In the most popular method of transferring liquid in the liquid chromatography, a plunger type pump is used and the transfer is performed by a reciprocating motion of the plunger. This generates a pulsating flow of the liquid being transferred, in accordance with the reciprocal motion of the plunger. In a conventional control method for eliminating the pulsations in the flow, a plurality of plungers are used in such a way that they react with each other to eliminate the pulsations. Nevertheless, this method has not achieved a complete elimination of pulsations in the flow.

Alternative methods of inserting an apparatus for the prevention of pulsating flow are known, in which the means used in the liquid transfer system is a flat pipe, a bellows, a spring, a combination of a bellows and a spring, or a combination of a diaphragm and a compressible liquid. Among the above-mentioned methods, that utilizing the change of volume of a flat pipe is effective only when the flat pipe is extremely long, which leads to the presence of a large dead volume causing extreme inconvenience when replacing the liquid. Further, a method using a bellows is effective only under a pressure of up to about 50 bar, and also is inconvenient when replacing the liquid due to a complicated configuration of the bellows. A method utilizing the elasticity of a spring is not effective in the low pressure range, and is inconvenient in that the rigidity and elasticity of the spring must be adjusted in accordance with changes in the liquid pressure. Further, a method using the combination of a bellows and a spring is effective to a certain extent from a low to a high pressure, but is still inconvenient in that the rigidity of spring must be adjusted.

Further, in an apparatus for the prevention of pulsating flow, such as disclosed in Japanese Unexamined Patent Publication No. 57-160060, in which one side of a flat flow path chamber is partitioned by a diaphragm and a sealed compression chamber enclosing a compressible liquid is provided facing the diaphragm, the volume of the compression chamber must be satisfactorily large in order to realize an effective prevention of pulsating flow, which necessitates a significantly large diaphragm, and as a result, makes it impossible to obtain a compact apparatus having a good performance for the prevention of pulsating flow in the liquid chromatograph.

In Japanese Unexamined Patent Publication No. 57-160060, a compression liquid chamber, which is used to prevent pulsating flow of a liquid being transferred at a reciprocation cycle of about 1 sec by a piston pump having a maximum capacity of 100 μl, is composed of a cylindrical portion having an aperture of 80 mm and a height of 88 mm and a conical portion having a depth of 10 mm and located below the cylindrical portion.

DISCLOSURE OF THE INVENTION

The present invention is intended to solve the conventional problems as mentioned above, and provides an apparatus for the prevention of pulsating flow in the liquid chromatograph, which has an excellent performance for the prevention of pulsating flow, a small dead volume, and an excellent operability, evenly throughout the whole region of from 5 to 400 bar of ordinary use for the liquid chromatograph.

An apparatus for the prevention of pulsating flow in the liquid chromatograph according to the present invention comprises a pressure vessel provided with a liquid transferring chamber partitioned by diaphragms on both flat sides thereof, and sealed compression chambers filled with a compressible substance and disposed facing said diaphragms.

If a compression chamber is provided on only one side of a liquid transferring chamber, only a single diaphragm will be used, and therefore, deformation of the diaphragm is doubled when a certain amount of transferred liquid is absorbed by the compression chamber. This inevitably doubles the volume of the compression chamber in order to stably retain the deformation, with the result that an apparatus for the prevention of pulsating flow must have an excessive size.

Further, a method according to the present invention is characterized in that, in an apparatus for the prevention of pulsating flow in the liquid chromatograph, (a) the total volume of two compression chambers is 50 to 300 ml, (b) the compressibility of the substance filled in the compression chambers is $(30 \text{ to } 200) \times 10^{-6}/\text{bar}$, (c) the ratio between the total volume of the two compression chambers and the total area of the two diaphragms is within a range of from 2 to 5 ml/cm², and the liquid transfer is performed according to the following relationship:

$$\Delta P \leq 5.0 + \alpha(P-50) \text{ and } 0 < \alpha \leq 0.1,$$

where P (in bar) represents a liquid transferring pressure within a range of from 5 to 400 bar, ΔP (in bar) represents a pressure fluctuation imposed on the liquid being transferred, and α is a positive parameter.

The ΔP/P value expressed in terms of the ratio between the above-mentioned ΔP and P is referred to as the flow pulsation ratio and is a principal index value for determining the characteristic for the prevention of pulsating flow. The conventional apparatus for the prevention of pulsating flow has a rather large ΔP relative to P, and therefore, usually is unable to operate under a pressure exceeding the region of the allowable flow pulsation ratio. On the contrary, the present invention ensures an excellent performance for the prevention of pulsating flow throughout the whole region of the liquid transferring pressure from 5 to 400 bar, which is ordinarily used in liquid chromatograph. The present inventors have established a proper relationship which concretely expresses the performance for the prevention of pulsating flow. The present relationship suggests that, in the region of a relatively lower liquid transferring pressure (P) from 5 to 50 bar, the pressure fluctuation ΔP is 5 bar or less and ΔP<<P, and that in the region where the liquid transferring pressure (P) exceeds 50 bar, the pressure fluctuation ΔP still does not exceed 10% of the liquid transferring pressure.

The flow pulsation ratio is determined by the relationship among various terms, such as the dimensions of the apparatus, the volumes of the parts of the apparatus, particularly of the compression chambers and the liquid transferring chamber,, the area of the diaphragms, and the elastic property of the elastic substance filled in the compression chambers, etc. The present inventors made intensive research into the relationships among these terms and, as result, derived the above-mentioned relationship between the liquid transferring pressure P and the pressure fluctuation $\Delta p$, this being expressed so as to enable determination of the index value of the flow pulsation ratio in relation to the condition that the total volume of the compression chambers is 50 to 300 ml, the ratio between the total volume of the compression chambers and the total area of the diaphragms is 2 to 5 ml/cm$^2$, and the compressibility of the substance filled in the compression chambers is $(30 \text{ to } 200) \times 10^{-6}$/bar, as mentioned above.

BRIEF EXPLANATION OF THE DRAWING

The present invention will be described with reference to the drawing, as follows. FIG. 1 shows a side view of an apparatus according to the present invention.

Figure 1:
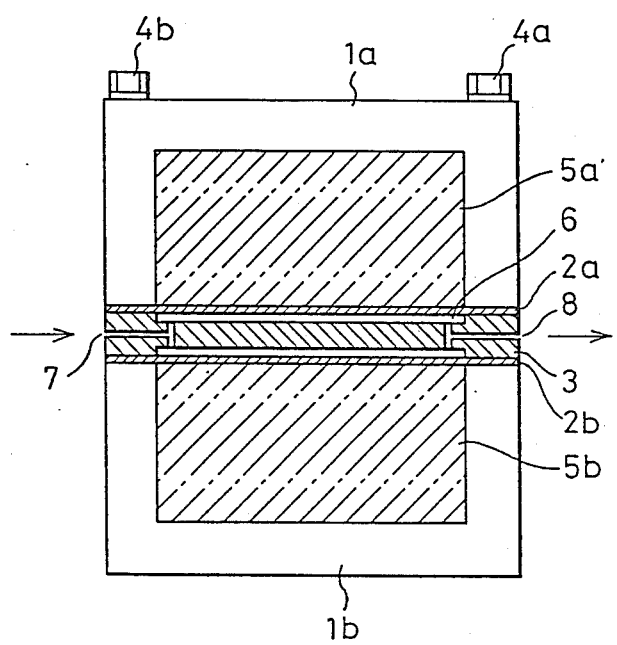
FIG. 1 is a sectional view of an apparatus according to the present invention.

Casings 1a and 1b are integrally combined by assembly bolts 4a and 4b to compose a pressure vessel, a flow path block 3 is provided with an inlet for liquid being transferred 7 and an outlet for liquid being transferred 8, and a liquid transferring chamber 6 is formed by diaphragms 2a and 2b and the flow path block 3. Compression chambers 5a and 5b are formed by the diaphragms 2a and 2b and the pressure vessels 1a and 1b. In these compression chambers 5a and 5b, a compressible substance, such as silicone rubber, which is a non-fluid rubber elastic body, etc., satisfies the aforementioned compressibility in the entire compression chambers 5a and 5b, and the volumes and the compressibilities of the compression chambers 5a and 5b are preferably substantially equal, respectively, to obtain an equivalent effect. A liquid transferring pipe from a plunger type pump is connected to the inlet for liquid being transferred 7, and a pipe to a separation column is connected to the outlet for liquid being transferred 8. The diaphragm 2a is arranged parallel with the diaphragm 2b so that pressure is uniformly distributed thereon. The liquid transferring block 3 extends over the central portion of the liquid transferring chamber in a direction from the inlet for liquid being transferred 7 to the outlet for liquid being transferred 8 to define the liquid transferring chamber 6 and to minimize dead volume. Flow paths branch out of the inlet for liquid being transferred 7 and the outlet for liquid being transferred 8, and communicate with the liquid transferring chamber 6.

A plunger used for the liquid chromatograph ordinarily transfers about 100 $\mu$l of liquid in one stroke, at a maximum. As the plunger moves in a reciprocal manner, e.g., reciprocates once in two seconds, a maximum of 100 $\mu$l of liquid is transferred in the first one second, and no liquid is transferred in the next one second. This cycle is continuously repeated. Thus, a pulsating flow at an interval of one second is generated in this case. When the thus transferred liquid passes through the present apparatus, the liquid flow increases and the pressure of the system rises during the plunger transferring stroke. As the pressure rises, the diaphragms 2a and 2b are pressed toward the compression chambers 5a and 5b, respectively, the non-fluid rubber elastic body filled in the compression chambers is compressed, and the pressure rise is alleviated. During the plunger non-transferring stroke, the compressed non-fluid rubber elastic body pushed back the diaphragms 2a and 2b to transfer liquid with the resulting alleviated pressure drop. Thus an elimination of pulsations in the flow is achieved.

As mentioned above, because the plunger pump used for the liquid chromatograph usually transfers a maximum of about 100 $\mu$l of liquid during a plunger transferring stroke, the pulsating flow can be prevented or mitigated if about 50 $\mu$l, a quantity equivalent to about a half of the maximum flow, can be absorbed by compression of the compression chambers, restraining a pressure rise to the smallest possible value, during the plunger transferring stroke. To this end, preferably the volume of the compression chambers are as large as possible, the compression chambers are filled with a compressible substance having as high a compressibility as possible, an diaphragms having an area and an elastic limit as large as possible are used.

However, if the volume of the compression chambers and the area of the diaphragms are large, a compact apparatus for the prevention of pulsating flow cannot be obtained. Further, numerous experiences in practical trials have led to a recognition that there are various limitations to the prevention of pulsating flow, due to the overall dimensions of the apparatus, the property of the material used for the apparatus, etc., in an apparatus for the prevention of pulsating flow used for the liquid chromatograph.

From the viewpoint of the actual size of the liquid chromatograph, the compression chambers preferably have a volume of 50 to 300 ml, more preferably within a range of 100 to 200 ml. If a volume of more than 300 ml is used, the compactness requirement cannot be met, and if a volume of less than 50 ml is used, a sufficient performance cannot be attained because of an insufficient capacity.

Experiences in practical trials have proved that the compressibility of a compressible substance filled in the compression chambers is sufficient if 50 $\mu$l of liquid can be absorbed at a pressure rise of 5 bar or so, which can be achieved by a compressibility of $(30 \text{ to } 200) \times 10^{-6}$/bar when the compression chambers have a volume within a range of 50 to 300 ml. Accordingly, an optimum compressibility is preferably selected in accordance with the size of the compression chambers. When the compression chambers have a total volume of 150 ml, and silicone rubber, which is a non-fluid rubber elastic body, is used as the compressible substance, 50 $\mu$l of the liquid being transferred is absorbed at a pressure rise of about 2 to 3 bar since silicone rubber has a compressibility of $(100 \text{ to } 150) \times 10^{-6}$/bar (when the liquid transferring pressure is 10 bar or more). This is a completely satisfactory performance for an apparatus for the prevention o pulsating flow used for the liquid chromatograph.

Although the diaphragm preferably has an area as large as possible, since deformation is thus minimized, this results in an enlargement of the dimensions of the apparatus for the prevention of pulsating flow, which then cannot meet the compactness requirement and also it becomes difficult technically to seal the compression chambers. If the area of he diaphragms is too small, there is a dagger that deformation will be so significant that it will exceed the elastic limit and cause a breakage of the diaphragms. An intensive study was carried out on metal diaphragms made of stainless steel or other materials most preferred in practice, and it was proved that a ratio between the volume of compression chambers and the area of diaphragms has an optimum range of 2 to 5 ml/cm$^2$.

Generally, a liquid transferring chamber has a volume about twice as large as the quantity of liquid being transferred.

BEST MODE FOR CARRYING OUT THE INVENTION

The relationship between the flow pulsation ratio (pressure fluctuation/liquid transferring pressure) and the liquid transferring pressure was obtained for an apparatus shown in FIG. 1 in which silicone rubber (compressibility: (100 to 150)$\times 10^{-6}$/bar) is filled in compression chambers (the invention) and for another commercially available apparatus in which a combination of a bellows damper and a spring is utilized (comparative example).

The quantity of transferred liquid was 2 ml/min, and the liquid transferring pressure was varied by connecting various columns. A plunger type pump was used to transfer 100 μl of liquid in one stroke, and the reciprocating motion was repeated 20 times in each trial. The compression chamber had a total volume of 100 ml, the diaphragms had a total area of 30 cm$^2$, and the liquid transferring chamber had a volume of 200 μl. The results are shown in Table 1. As is obvious from Table 1, an apparatus according to the present invention realizes a reduced flow pulsation ratio evenly over the whole region of the tested liquid transferring pressure, and realizes a pressure fluctuation of 5% or less over the whole region.

TABLE 1

| Liquid Transferring Pressure | | 50 | 100 | 200 | 350 |
|---|---|---|---|---|---|
| Flow Pulsation Ratio (%) | Present Invention | 5 | 4 | 3 | 2 |
| | Comparative | 32 | 20 | 17 | 15 |

TABLE 1-continued

| Liquid Transferring Pressure | 50 | 100 | 200 | 350 |
|---|---|---|---|---|
| Example | | | | |

CAPABILITY OF EXPLOITATION IN INDUSTRY

As described above, an apparatus for the prevention of pulsating flow in liquid chromatography according to the present invention has an excellent performance as an apparatus sufficiently effective for the prevention of pulsating flow, and also has the advantages of an excellent operability and small dead volume, because the compression chamber, the diaphragm, and other components have simple shapes.

We claim:

1. Apparatus for the prevention of pulsating flow in a liquid chromatograph comprising:
   a pair of pressure vessels each having an open side and a hollow interior,
   a liquid flow block disposed between said vessels and having a recess in opposite faces thereof defining a pair of liquid transfer chambers,
   liquid passage mean extending from opposite ends of said block to said transfer chambers respectively,
   a pair of resilient diaphragms disposed in overlying engagement with said opposite faces of said block respectively and in engagement with said pressure vessels to define a sealed pressure chamber in the interior of each vessel and a compressible substance completely filling each of said pressure chambers.

2. Apparatus for the prevention of pulsating flow ion the liquid chromatograph according to claim 1, characterized in that a total volume of said two compression chambers is 50 to 300 ml, a compressibility of said compressible substance filled in said compression chambers is 30 to 200$\times 10^{-6}$ /bar, a ratio between said total volume of said two compression chambers and a total area of said two diaphragms is within a range of from 2 to 5 ml/cm$^2$.

* * * * *